US010303851B2

(12) United States Patent
Nguyen et al.

(10) Patent No.: US 10,303,851 B2
(45) Date of Patent: May 28, 2019

(54) PHYSICIAN-CENTRIC HEALTH CARE DELIVERY PLATFORM

(71) Applicant: MD24 Patent Technology, LLC, Surprise, AZ (US)

(72) Inventors: Linh C. Nguyen, Peoria, AZ (US); An-Dien Nguyen, Fremont, CA (US); Khiem Allen Le, Orange, CA (US)

(73) Assignee: MD24 Patent Technology, LLC, Surprise, AZ (US)

( * ) Notice: Subject to any disclaimer, the term of this patent is extended or adjusted under 35 U.S.C. 154(b) by 227 days.

(21) Appl. No.: 14/212,254

(22) Filed: Mar. 14, 2014

(65) Prior Publication Data

US 2014/0276552 A1    Sep. 18, 2014

Related U.S. Application Data

(60) Provisional application No. 61/791,590, filed on Mar. 15, 2013.

(51) Int. Cl.
| | |
|---|---|
| *G16H 50/20* | (2018.01) |
| *G06F 19/00* | (2018.01) |
| *A61M 37/00* | (2006.01) |
| *A61M 5/172* | (2006.01) |
| *A61M 5/142* | (2006.01) |
| *A61B 5/00* | (2006.01) |

(52) U.S. Cl.
CPC ..... *G06F 19/3418* (2013.01); *A61M 5/14248* (2013.01); *A61M 5/1723* (2013.01); *A61M 37/0015* (2013.01); *G16H 50/20* (2018.01); *A61B 5/0022* (2013.01); *A61M 2037/003* (2013.01); *A61M 2037/0023* (2013.01); *A61M 2037/0046* (2013.01); *A61M 2205/0244* (2013.01); *A61M 2205/3303* (2013.01); *A61M 2205/3553* (2013.01); *A61M 2205/52* (2013.01); *A61M 2230/005* (2013.01)

(58) Field of Classification Search
CPC ....... G06F 19/3418; G06F 19/322–327; G06F 19/00; G06Q 50/22–24; G16H 50/20
USPC .......................................................... 705/3
See application file for complete search history.

(56) References Cited

U.S. PATENT DOCUMENTS

| | | | | |
|---|---|---|---|---|
| 6,039,688 | A * | 3/2000 | Douglas | ............. G06F 19/3475 128/921 |
| 7,941,327 | B2 | 5/2011 | Brown | |
| 2003/0171710 | A1* | 9/2003 | Bassuk | ............... A61M 31/002 604/67 |

(Continued)

*Primary Examiner* — Sheetal R Paulson
(74) *Attorney, Agent, or Firm* — The Webostad Firm, A Professional Corp.

(57) ABSTRACT

A system for diagnosing and/or treating a patient comprising a patient information database for storing and retrieving patient health data related to the patient. The data includes one or more of real-time patient health information, at least one clinical practice guideline, at least one patient questionnaire and a patient medical history. At least one server is operative to access the patient information database. A computing device remotely located from the server, including a microprocessor, configured to store a computer application and is configured for communication with the server for retrieving of the patient health data. The computer application generates at least one of a patient diagnosis or a patient treatment recommendation using the retrieved patient health data.

14 Claims, 9 Drawing Sheets

(56) References Cited

U.S. PATENT DOCUMENTS

| | | | |
|---|---|---|---|
| 2007/0244724 A1* | 10/2007 | Pendergast | G06F 19/3418 |
| | | | 705/3 |
| 2008/0287922 A1* | 11/2008 | Panduro | G06F 19/3456 |
| | | | 604/890.1 |
| 2011/0288884 A1* | 11/2011 | Algoo | G06Q 50/01 |
| | | | 705/3 |
| 2014/0058742 A1* | 2/2014 | Chari | G06F 19/345 |
| | | | 705/2 |
| 2014/0324020 A1* | 10/2014 | Stefansen | A61B 5/14532 |
| | | | 604/506 |

* cited by examiner

PHYSICIAN-CENTRIC HEALTH CARE DELIVERY PLATFORM

CROSS-REFERENCE TO RELATED APPLICATIONS

The present application claims the benefit of U.S. Patent Application No. 61/791,590, filed Mar. 15, 2013, which is hereby incorporated by reference in its entirety.

FIELD OF THE INVENTION

The present invention is directed toward providing a physician-centric health care delivery system which addresses the medical needs of non-hospitalized patients while implementing state-of-the-art technologies in remote telehealth/telemedicine monitoring (RTM) and drug delivery systems. The systems may further include personal care visits by a member of a house call physicians network, as needed, to further reduce readmissions and health care cost in rural areas. The drug delivery system may be monitored and accessed from a remote location as well.

BACKGROUND OF THE INVENTION

A current health care delivery model for elderly patients in rural communities is nonexistent. As a result, primary care physicians are unable to handle the increasing numbers of retiring baby boomers in these rural communities. While telehealth and telemedicine implemented by a nurse-centric model has been used to address this problem, these efforts have failed to show a significant reduction in hospital readmissions or overall healthcare costs.

For example, in 2012, Intel and the Mayo Clinic jointly performed an extensive study of the effectiveness of a nurse-centric model used in conjunction with remote telehealth/telemedicine monitoring ("RTM"). A randomized controlled trial was performed among adults aged older than 60 years at high risk for rehospitalization. Participants were randomized to RTM (with daily input) or to patient-driven usual care. RTM was accomplished by daily biometrics, symptom reporting, and videoconference. Among older patients at the end of the study, RTM with a nurse-centric model did not result in fewer hospitalizations or emergency room ("ER") visits.

The basic premise of the physician-centric health care delivery system used in conjunction with RTM, as opposed to a nurse-centric system used in conjunction with RTM, is that physicians can dramatically reduce ER and hospital admissions/readmissions better than nurses, especially when the health care is provided in a home care or nursing home care setting. There are two practical reasons for this. First, in a nurse-centric system used in conjunction with RTM, because of the liability, a patient recently discharged from a hospital frequently will be unnecessarily sent back to an ER by a nurse after analyzing the RTM data. Further, the nurse analyzing the data may not know the patient's medical history as thoroughly as a physician who has access to the patient's electronic health record ("EHR"). Yet further, because a nurse cannot readily order lab tests or prescribe medications, and typically does not carry individual malpractice insurance, a nurse may not be willing to assume the liability risk for erroneously opting for home treatment rather than hospitalization. On the other hand, a trained physician can more readily assess the symptoms presented by the data, order lab tests and a chest x-ray if needed (or perhaps simply modify medications), thereby saving the costs relating to an ER visit, or hospital admission or readmission. Moreover, in the event that hospital admission is warranted, the physician can admit the patient directly to the hospital whereas, typically, a nurse does not have admitting rights and would have to, instead, redirect the patient to the ER for hospital admission.

Secondly, a physician may be afforded a better opportunity to offer to a patient the hospice alternative to hospital admission. Patients with late-term illnesses may often bounce between hospital discharge and hospital readmission on a weekly cycle. A physician with influence over the patient's medical power of attorney may be able to offer patients the hospice alternative at the appropriate time to break this cycle and lessen the cost of repeated hospitalization.

Several cost benefits of a physician-centric model used in conjunction with RTM are apparent. Once a patient appears in the ER without a prior diagnosis by a treating physician, the risk imposed on an ER physician for prematurely discharging the patient from the hospital may cause patients to be unnecessarily admitted instead. Once admitted, unnecessary costs of additional tests performed by the hospital may be incurred. If these visits to the ER can be reduced by the intervention of a treating physician using RTM, the costs relating to the admission and tests may be avoided. In addition, in a physician-centric model used in conjunction with RTM in accordance with the invention, the treating physician is available 24/7, as needed. This means that the treating physician can analyze patient data and interpret test results close to real-time and therefore can administer patient care quickly, thereby reducing the urgency of a patient to appear in the ER for treatment.

Thus, there is a need for a physician-centric health care delivery system for patients, particularly elderly patients in rural communities, which implements state-of-the-art technologies in telemedicine. This system may be combined with personal care visits by a member of a house call physicians network or patient visits to a satellite/mobile facility such as, for example, a free standing medical clinic, an office building, a room in an office or a kiosk, to further reduce readmissions and health care costs. This system incorporates a physician-based clinical decision support system ("PCDSS") integrated with a remote telehealth/telemedicine monitoring (RTM) platform that is capable of analyzing and diagnosing the medical condition of a patient and/or administering health care to a patient in real-time while also providing the treating physician with recommended treatment options. In a further embodiment, the physician-centric health care delivery system includes a "smart" delivery device capable of automatically administering medications to a wearer of the device. The "smart" delivery device may be further adapted to communicate remotely with a physician so that the physician can modify the amount or type of drug being delivered. The present invention addresses these and other needs.

BRIEF SUMMARY OF THE INVENTION

In one aspect, the present invention is directed to a system for diagnosing and/or treating a patient comprising a patient information database for storing and retrieving data related to the patient. Data includes one or more of real-time patient health information, at least one clinical practice guideline, at least one patient questionnaire and a patient medical history. Also provided is at least one server operative to access the patient information database. A computing device is remotely located from the server and includes a microprocessor configured to store a computer application. The computing device is configured for communication with the server for retrieving the patient health data and the computer application generates at least one of a patient diagnosis or a patient treatment recommendation using that retrieved patient health data. In another aspect, the present invention is directed to a method for diagnosing and/or treating a patient. The method comprises the steps of: providing a patient information database for storing and retrieving data related to the patient; providing at least one server operative to access the patient information database; providing at least one computing device remotely located from the server where the computing device includes a microprocessor configured to store a computer application and wherein the computing device is configured for communication with the server; providing the patient with a remote telehealth/telemedicine device to generate real-time patient health information; storing the real-time patient health information in the patient information database; and generating at least one of a patient diagnosis or a patient treatment recommendation using the computer application based upon the real-time patient health information.

In a further aspect, the present invention is directed to a system and method for automatic and remotely controlled administration of drugs or other medications. The system utilizes a "smart" delivery system having control circuitry in communication with an actuator for dispensing medications and onboard sensors for monitoring patient health, while also being wirelessly connected to a smart phone or other smart device or any other suitable wireless hub to download device data and upload physician instructions.

Additional objects, advantages and novel features of the present invention will be set forth in part in the description which follows, and will in part become apparent to those in the practice of the invention, when considered with the attached figures.

DETAILED DESCRIPTION OF THE INVENTION

Generally, the system and method described provides for a physician-centric health care delivery system which addresses the needs of non-hospitalized patients, such as for example, elder patients living at home or in a nursing care facility. The system and method includes state-of-the-art technologies relating to RTM and may be implemented in hardware, software or a combination thereof, and may be distributed across a variety of computing devices.

The present invention provides a physician-centric health care delivery system and method which addresses the needs of patients, particularly the elderly, while implementing state-of-the-art technologies in telemedicine. In one aspect of the invention, the system further includes personal care visits by a member of a house call physicians network or patient visits to a regional, mobile or other designated care giving facility to reduce readmissions and health care costs, particularly for elderly patients in rural areas. In a further aspect of the invention, a patient is equipped with a programmable drug delivery device to deliver medications when scheduled or when conditions indicate need for drug intervention.

Figure 1:
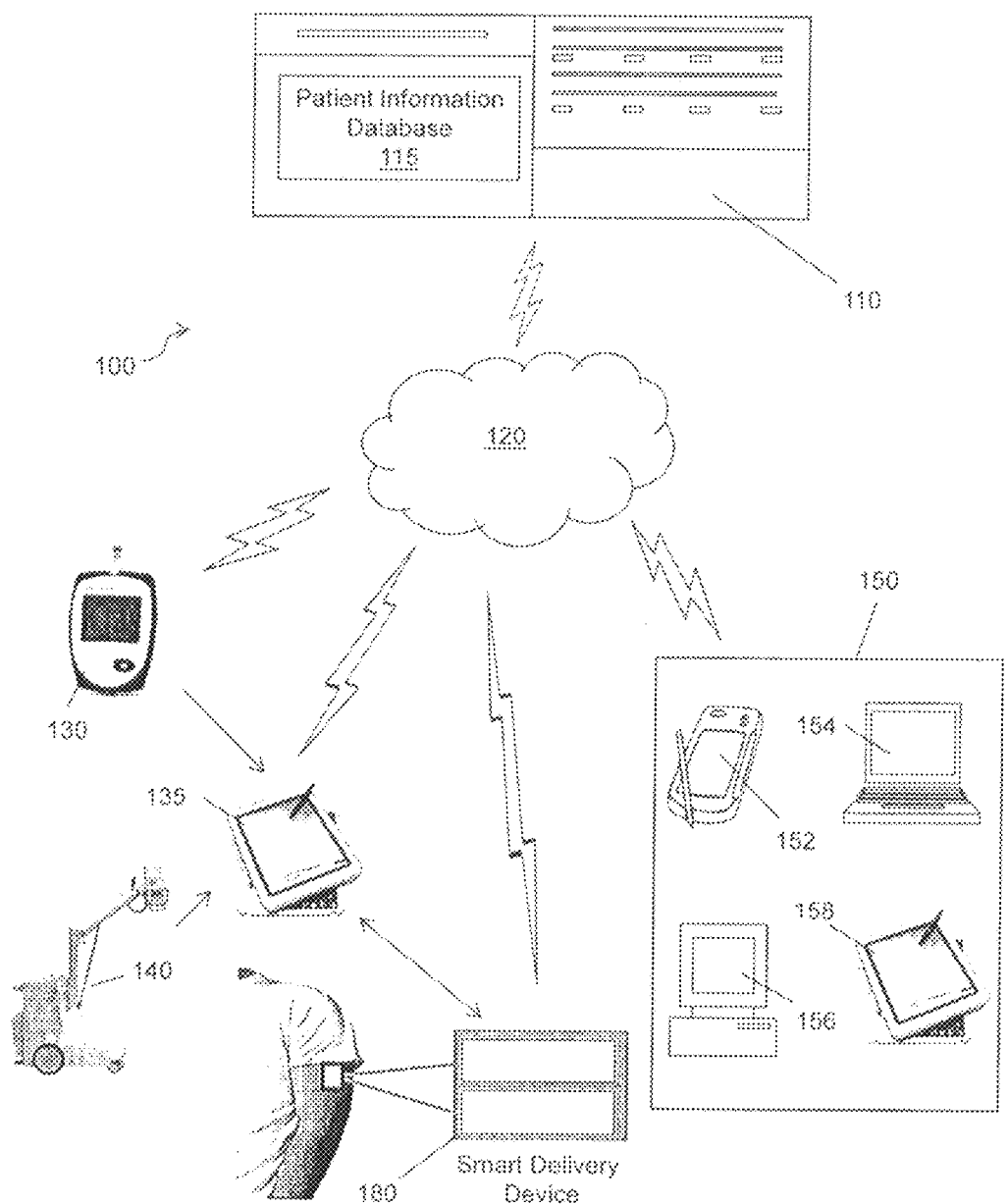
FIG. 1 is a general schematic of a physician-centric clinical decision support system according to one embodiment of the present invention.

Referring to the drawings in detail, and initially to FIG. 1, a physician-centric health care delivery system incorporating a physician-centric clinical decision support system ("PCDSS") according to one embodiment of the present invention is provided and identified as reference number 100. System 100 generally includes an internet accessible server 110 in communication with the internet 120. The server 110 is operative to access a patient information database 115. Patient information database 115 stores and retrieves data related to a patient and may include real-time patient health information, one or more clinical practice guidelines and patient medical history/questionnaire responses. To populate patient information database 115 with patient data, as well as to monitor and treat patients, each patient (for example a patient indicating heart-failure) will receive a device 130 equipped to provide remote telehealth/telemedicine monitoring ("RTM"). The RTM device allows a patient to take his or her vital signs and other medical data as ordered by a physician (e.g., blood glucose levels, blood pressure, oxygen saturation, weight, etc.) from the comfort of the patient's home or residence within a nursing care facility. The data may be entered manually by the patient or may be measured and recorded automatically by the device. The patient health data measured by the RTM device may be enabled for wireless communication with server 110, or the data may be loaded onto a computing device 135 for uploading to the server. Examples of such computing devices include but are not limited to a smart phone, a laptop computing device, a personal computing device, a tablet computing device/iPad, other smart devices or other suitable data hub device. Computing device 135 may also enable patients to complete online questionnaires regarding their health, as well as allowing patients to view their medical chart/history. Computing device 135 may further enable communication between patients and physicians through use of electronic mail and/or video conferencing, such as Skype, FaceTime, Vring and the like. In accordance with the invention, computing device 135 has stored within its memory a videoconferencing software application, and more preferably this application enables the computing device to conduct videoconferencing through Skype due to Skype's large user population and available public application programming interface. In a further embodiment discussed in detail below, a patient is fitted with a "smart" delivery device 180 which automatically dispenses medication to the patient. Smart delivery device 180 may further act as a hub and be enabled for wireless communication with computing device 135 or communication over network 120.

In preferred embodiments, the physician-centric health care delivery system platform is a web-based application that physicians can access anywhere through a wired or wireless connection, such as over the internet or by using a 4G-enabled mobile device like an iPhone iPad or Android phone; tablet computing device. By utilizing a web-based system, a treating physician can use the PCDSS application to access the patient information database 115 (via server 110) from any internet accessible location using an internet enabled computing device 150. Examples of suitable computing devices include a smart device, such as smart phone/PDA/iPhone 152, laptop computer 154, personal computer (PC) 156, and tablet PC or iPad 158. The PCDSS application assists physicians in providing an accurate diagnosis of a patient's medical condition based on patient data from the patient information database 115 such as the electronic health record (EHR)/Patient Health Record (PHR), daily data from RTM devices and patient questionnaires/medical history. Relevant patient data from the patient information database 115 (patient history, previous encounter history, drug allergies, age, weight, etc.) and other updated daily data (heart rate, blood pressure (BP), weight, oxygen saturation, etc.) provide the necessary input for the PCDSS analytical engine to suggest appropriate diagnostic and treatment options that physicians can review and modify if needed.

If indicated by a patient's condition as monitored via RTM, mobile medical support professionals (e.g. a home health nurse or nurse practitioner) may conduct additional medical tests using mobile medical device 140 at the patient's home, nursing care facility or other suitable locations, such as for example, a medical clinic, or a satellite/mobile facility such as an office building, a room in an office or a kiosk, without requiring the patient to be taken to, and possibly being admitted into, a hospital. Examples of additional medical tests may include a portable x-ray, ultrasound, mobile echocardiography, and on-site blood analyses. As with the RTM device, mobile medical device 140 may be enabled for wireless communication with server 110, or the data generated by the device may be loaded onto a computing device 135 for uploading to the server. Patient health information communicated to server 110 is stored within a patient's designated individual Patient Health Record within patient information database 115. Preferably, a notice is automatically provided to the physician informing the physician that additional medical information is available for review within the patient information database 115 once that information is loaded onto the server. Further, as will be discussed in greater detail below with regard to FIG. 2, the PCDSS incorporates any additional information into its algorithm and produces updated diagnoses and/or treatment options for review by the physician.

Figure 2:
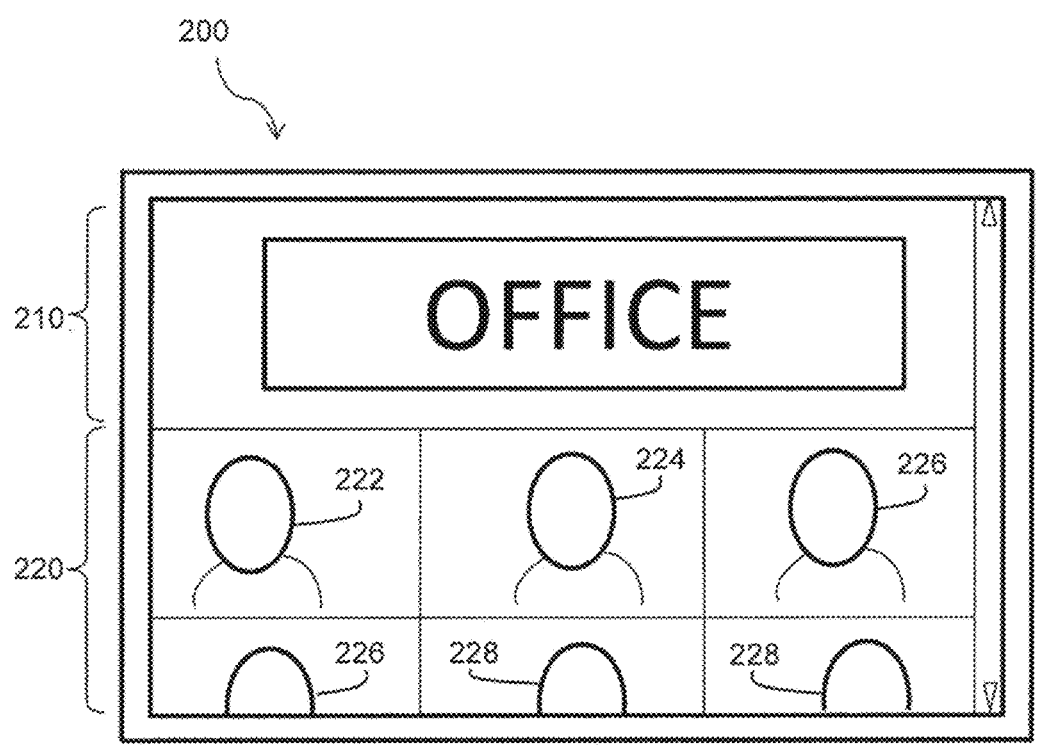
FIG. 2 is a schematic diagram of a patient screen display using a videoconferencing software application according to one embodiment of the present invention.
Figure 3:
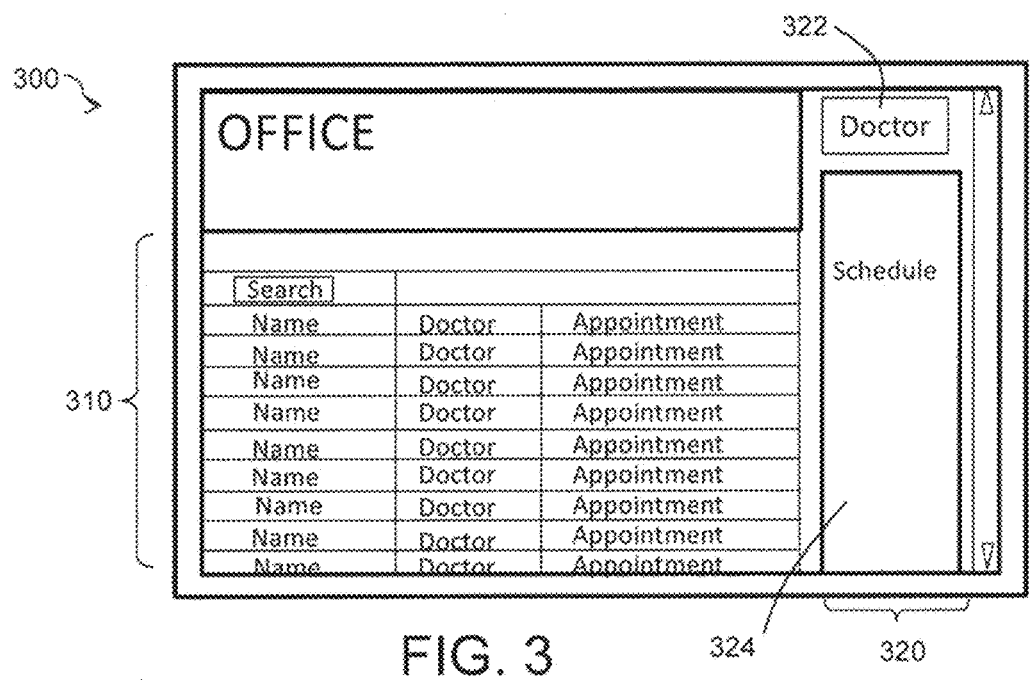
FIG. 3 is a schematic diagram of an administrator screen display using a videoconferencing software application according to one embodiment of the present invention.
Figure 4:
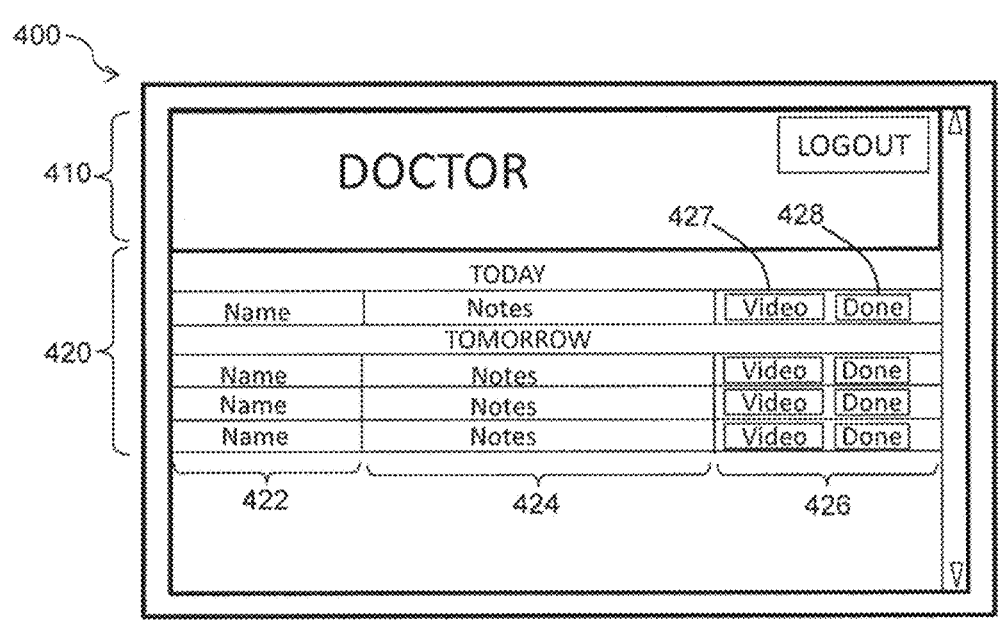
FIG. 4 is a schematic diagram of a physician screen display using a videoconferencing software application according to one embodiment of the present invention.

Turning now to FIGS. 2-4, shown are generalized schematics of screen displays using a videoconferencing software application according to one embodiment of the present invention. With regard to FIG. 2, patient screen display 200 will generally be viewed by a patient using computing device 135 when running the videoconferencing software application of the present invention. As seen in FIG. 2, patient screen display 200 is divided into two regions 210 and 220. Region 210 provides a one-touch link to the office of the treating physician. Activating this link, whether by mouse click, touchscreen or other action, causes the videoconferencing software to initiate a videoconference call to the physician's general office computing device. This call will be answered by an office administrative assistant or other staff who will then, for instance, assist the patient in setting up an appointment to conference with a physician or instruct the patient to waft on the line before transferring the videoconference to the physician's computing device. Region 220 provides one-touch links to specific individuals which may include the patient's treating physician 222, primary care physician 224 or any specialists 226 involved in that patient's treatment. Activation of any of these links will directly initiate a conference call to the selected physician's computing device. Region 220 may also include links to individuals 228 who have been diagnosed and/or treated for the same medical condition afflicting the patient. Activation of any of these links allows for social interaction between patients so as to form a virtual support group. It is further envisioned that additional pages may be displayed within the videoconferencing software application, including but not limited to a page wherein a patient can view a physician's schedule and thereby arrange an appointment for a videoconferencing, a page containing a digital copy of the patient's calendar showing upcoming appointments or other relevant information and a page including links to journal articles or other items of news relevant to the patient's condition or treatment.

FIG. 3 shows a generalized screenshot 300 of the videoconferencing software application viewed by administration personnel within the physician's office. Screen region 310 displays the name, treating physician, and scheduled appointment time, preferably in chronological order with the next client appointment in time displayed as the top entry with each subsequent appointment listed below. Box 312 permits the administrative personnel to search for a particular patient. Thus, if patient Q cannot remember or locate the time of her next appointment, the software application allows administration to search and locate that patient Q's next appointment date and time. Region 320 displays information specific to a particular physician/doctor. Box 322 provides a drop-down menu wherein administration personnel can select a particular doctor and have that doctor's daily schedule appear in box 324. Thus, if a patient contacts the office through a videoconference link (activation of region 210) for an unscheduled conference, office personnel will be able to determine if the doctor is free to engage in that conference or whether the doctor is otherwise occupied. Box 324 also enables office personnel to efficiently schedule appointments for the various physicians within the office.

Turning now to FIG. 4, screen display 400 is a username and password protected application page accessible only to a particular physician. Once logged onto her videoconference page, physician "DOCTOR" (as shown in region 410) is presented with a listing of upcoming scheduled videoconference appointments as displayed in region 420. Each horizontal patient line within region 420 provides for the patient's name and time of appointment, and in preferred embodiments a synopsis of relevant case information, (422), a type-in section wherein the physician can input notes regarding topics or areas to be discussed during the call (424), and a contact region 426 having one-touch video activation links 427 which, when mouse-clicked or touch operated, etc., either initiate a videoconference call or consummate a videoconference call already initiated by the patient. Clicking or otherwise engaging "Done" link 428 ends the videoconference and instructs the videoconferencing software application to save a copy of the videoconference to a remote server or other archive for later use or referral, if needed.

A further embodiment of the present invention utilizes advancements in microcontroller and microfluidics technologies to equip patients with "smart" drug delivery devices for RTM and remote treatment. Smart drug delivery devices can be segregated generally into three broad categories. The first category includes intravenous ("IV") devices where a physician has direct access to a patient's bloodstream through an IV port. Coupled to this port is the smart delivery device. IV devices provide for the quickest administration of medication as these drugs are injected directly into the bloodstream and do not require diffusion through the skin or other tissues. These devices are best suited for cases involving threats of severe and immediate loss of health, such as high risk heart attack or stroke patients. While IV devices provide the quickest delivery, these systems are not always available to remote patients.

Thus, a second category of smart delivery devices include those for subcutaneous ("SC") administration. These smart devices generally include needles of sufficient gauge and length which puncture the skin and dispense drugs within the subcutaneous or muscle layers of the patient. Again, SC smart delivery systems are best suited for conditions which require only periodic or immediate administrations as repeated punctures will lead to increased pain at the injection site and decreased patient compliance.

The third category of smart delivery devices are those designed for transdermal ("TD") administration. These devices utilize microneedles to penetrate the skin to a depth generally less than 1 millimeter thereby bypassing the moisture barrier of the outer skin without impinging upon the nerves located within the dermis layer of the skin. Thus, TD devices are pain free but suffer from the fact that administered drugs must still pass through the dermis layer before entering the blood stream. As such, these smart devices are best suited for applications which require non-immediate and repeated dosing.

To fully capitalize on each of the three approaches, the smart delivery devices of the present invention not only utilize single injection systems with one needle or one supply channel, but also employ advances in microfluidics and utilize microfluidic chips engineered with an array of microtubules to deliver drugs to the needles. These microtubule arrays expand drug delivery from simply one needle/ one drug to one array/multiple drugs. These arrays are simply mated to ensure fluid communication between the microtubule and the needle (whether IV, SC, or TD microneedles). Thus, the smart delivery devices of the present invention are readily adapted to combination drug therapy using a single device.

Figure 5:
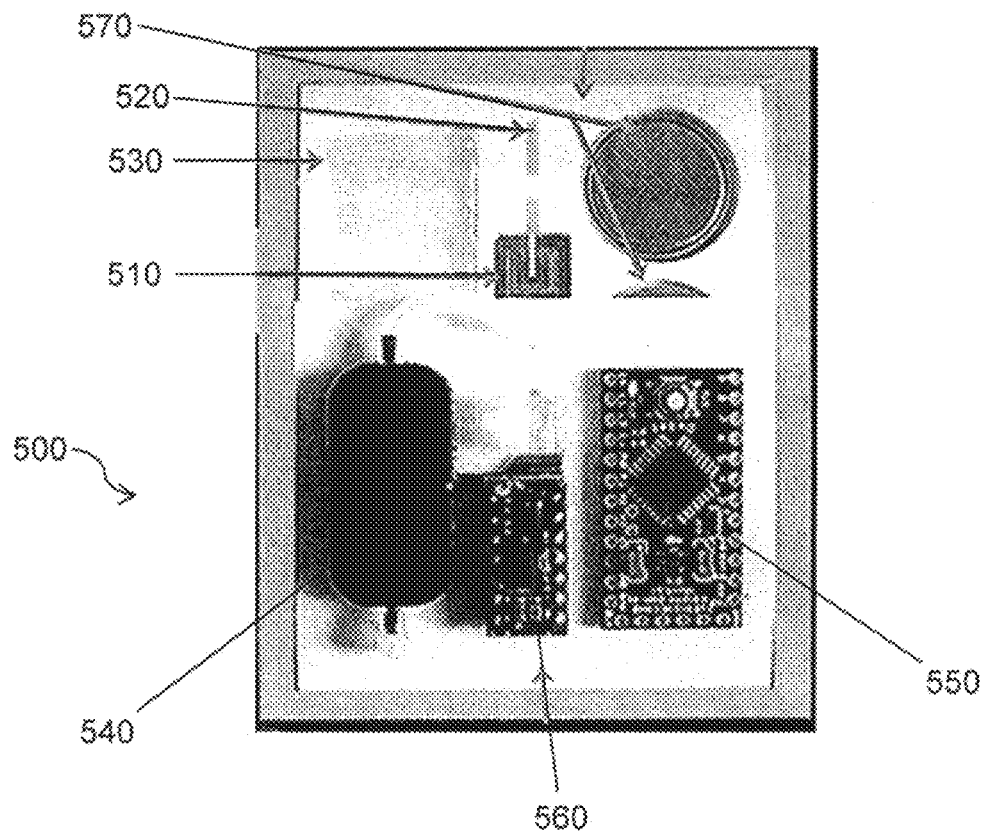
FIG. 5 shows a first embodiment of a smart delivery device according to the present invention.
Figure 5A:
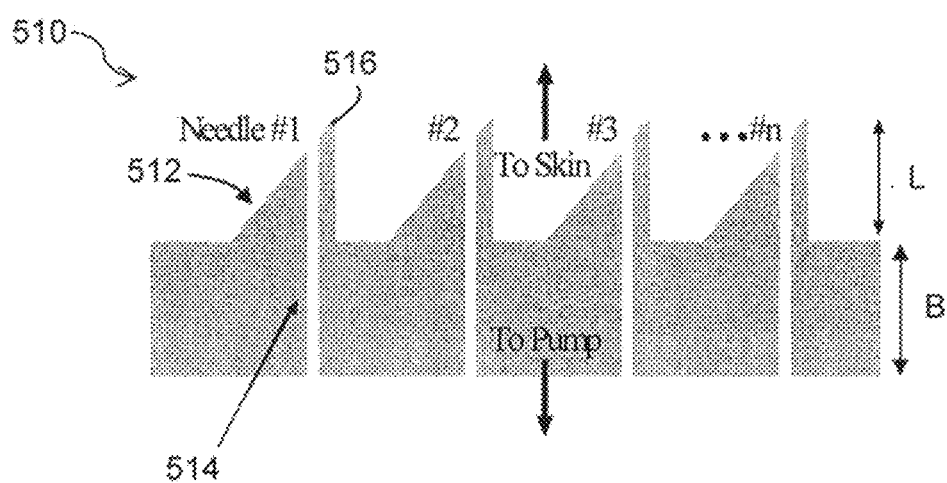
FIG. 5A is a representative side view of a microneedle array used in an embodiment of a smart delivery device according to the present invention.

An example of a smart delivery device for TD drug administration is shown generally in FIGS. 5, 5A, 6A and 6B as a transdermal patch. Transdermal patch 500 shown in FIG. 5 has a bottom surface which is adapted to carry an array of microneedles 510 whereby the needles are position so as to puncture the skin when the patch is worn. A general schematic view of an array is shown in FIG. 5A. Each microneedle 512 within the array 510 has an out-of-plane design with the bore 514 of each needle displaced from the needle tip 516 so that each needle is able to penetrate and exit the skin without tissue or fluids plugging the bore. Needle length L is selected to be between 100 microns and 500 microns, and preferably between 150 microns and 350 microns, and even more preferably are 350 microns. The base of the array which supports the needles has a thickness B of about 250 microns. However, arrays may be constructed to have bases of any suitable thickness depending on their application and the requirements imposed by the remaining components of the delivery device. Bore 514 has a bore diameter of roughly 50 microns to 100 microns, and more preferably about 70 microns. The bore extends proximate tip 516 through the entire length of the needle L and base B. Each microneedle is serially selectively fed a medication for injection through microfluidic channel 520. This medication is pumped from drug reservoir 530 through channel 520 by provision of dual-stage micro piezo pump 540 whose operation is controlled by microcontroller 550. Suitable drive electronics 560 manipulate channel 520 position relative to a particular microneedle within the microneedle array to ensure that each microneedle is used for a single injection. The mechanical components of the patch are powered by one or more batteries 570. In accordance with the invention, TD patch 500 is constructed as a two-piece system wherein a reusable first piece secures the microcontroller, drive electronics and dual-stage pump and a disposable second piece contains the batteries, microfluidic channel, drug reservoir and microneedle array.

Figure 6A:
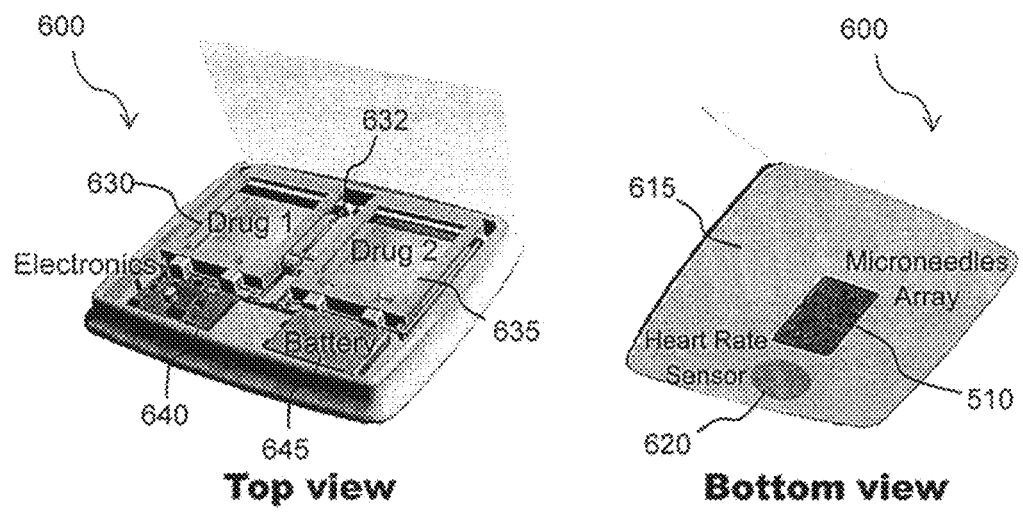
FIG. 6A shows a second embodiment of a smart delivery device according to the present invention.

An alternative transdermal patch design is shown in FIG. 6A as TD patch 600. TD patch 600 is similar to TD patch 500 but has been expanded to include a dual channel design employing two drug reservoirs 630 and 635. Respective microchannels 632 deliver fluid from each drug reservoir to a particular microneedle within microneedle array 510. By employing more than one reservoir, the embodiment of TD patch 600 allows a physician to begin to introduce combination drug therapy by administration of two different drugs, each contained within its own reservoir. Alternatively, one reservoir may contain a prescribed medication while the second reservoir contains a chemical enhancer to assist drug absorption through the skin (as discussed in more detail below). Fluid flow is controlled through micro-actuators, although micro piezo pumps may also be used.

A microcontroller and associated electronics 640 controls dispensing of drugs, with one or more batteries 645 supplying electrical power to the patch components. The microcontroller can be programmed to initiate dispensing of drugs from the drug reservoirs at a predetermined dosage at a predetermine time interval. In accordance with the invention, TD patch 600 is further equipped with a medical sensor 620, for instance a heart rate sensor. If preprogrammed by the physician, data received by the microcontroller from the sensor (in other words, data transmitted from the sensor to the microcontroller) may cause the microcontroller to activate the drug delivery mechanism upon a triggering event detected by the sensor. The dual channel design has a cost-effective two-layer construction with a first layer including (electronics, pump and rechargeable battery) and a disposable bottom layer housing the microfluidic delivery channels, microneedles, and dual refillable drug reservoirs and a soft rubber adhesive backing 615. TD patch 600 is very small measuring approximately 5 cm×6 cm×0.7 cm, non-intrusive, wearable under loose clothing, and is a refillable and re-useable electronics drug delivery vehicle.

Figure 6B:
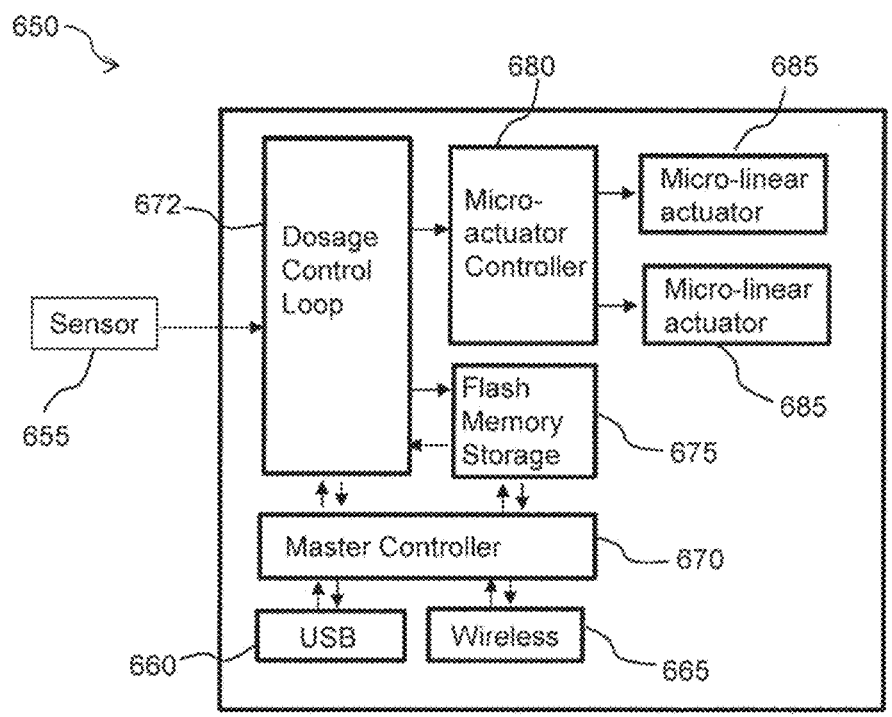
FIG. 6B shows a third embodiment of a smart delivery device according to the present invention.

A third transdermal patch for smart drug delivery is schematically represented as TD patch 650 in FIG. 6B. TD patch 650 is a smart and highly-responsive multifunctional transdermal patch device with closed loop feedback control that can provide a treatment that is dynamically tailored to patient's condition and input. Electronic control circuitry interfaces with dual micro-linear actuators for drug delivery. In accordance with the invention, a heart rate monitoring sensor and other sensor devices 655 communicate (i.e. transmit) real-time data to the patch through wire connection (i.e. USB) 660 or via a wireless networking infrastructure 665. For instance, the heart rate monitoring sensor data can be used to provide real-time adjustment to the drug delivery rate reflecting circadian rhythm adjustment throughout the day for minimum side effect and optimum impact based on the allowable range of therapeutic drug levels required by a health provider's prescription. As opposed to the patches shown and described with regard to TD patches 500 and 600, TD patch 650 replaces the patch electronic control circuitry with a more advanced microcontroller 670. The microcontroller runs firmware that contains the actuator control loop dispensing 672 for the drug(s) to be administered. TD patch 650 also contains a wired (USB) 660 and/or wireless interface 665 to facilitate remote communication with the patch for reconfiguration and programming of dosages which incorporates a closed loop algorithm. In accordance with the invention, the closed loop algorithm adjusts dosages by taking into account heart rate variable and circadian relationship. Flash memory storage 675 is included to periodically store the sensor readings and build a treatment history. TD patch 650 also contains additional components such as a micro-actuator controller 680 and one or more micro-actuators 685 and drug formulation reservoir(s) and microneedle array (not shown) similar to those described above with regard to TD patch 600.

In accordance with the invention, when a smart phone or other smart device is connected (through USB port or wirelessly) to TD patch 650, patient feedback information, sensor data (i.e. heart rates) and delivered dosage data will be collected and securely uploaded from the smart phone/device to the patient information database 115 (see FIG. 1). Alternatively, this data may be directly uploaded from the TD patch 650 to the patient information database 115 through wireless communication. Health care professionals can then review the updated patient data in the database and, if needed, remotely send a new delivery profile to the smart phone/device. This updated delivery profile will be transferred to patch 650 and activated the next time the smart phone/device is connected to the patch. Through this feedback system, doctors will have the capability to remotely monitor patient status and remotely change, if needed, the frequency and rate of drug delivery. In a further embodiment, TD patch 650 may automatically deliver medications upon sensor readings indicating an immediate need. For instance, sensor 655 may record readings indicating the patient is having a potential heart attack. If these sensors readings correspond to a minimum threshold incorporated within the closed loop algorithm, the microcontroller instructs the micro-actuator controller to cause the micro-actuators to dispense an immediate dosage to prevent or minimize damage due to the sensed potential heart attack.

An important consideration to keep in mind when utilizing transdermal drug delivery systems is the need for chemical enhancers to assist the diffusion of administered drugs through the skin to the bloodstream. Chemical enhancers such as oleic acid have been used for decades. Many such compounds, however, are toxic (such as DMSO or dimethyl acetamide). Furthermore, many of these enhancers are useful either only for a limited number of drugs or irritate the skin. More recently, combinations of non-toxic chemicals have been found that are effective for a wide variety of drugs without causing irritation. Normally the number of formulations to test was so large that it made testing mixtures difficult. However, a recent advance (impedance guided high-throughput screening) has made such testing feasible. Two particularly promising chemical enhancer mixtures are N-lauroyl sarcosine:sorbitan monolaurate (NLS:S20) and sodium laureth sulfate:phenyl piperazine (SLA:PP).

A further factor to be considered during transdermal drug administration is the function of time and the natural circadian rhythm. Indeed, the ability to deliver medication dosages that vary as a function of time, particularly to understand and effectively treat addiction may prove to be critical. For some addictive drugs, such as heroin and cocaine, the very short time between administration and the resulting "peak" effects of the drug is a key contributor to their addictive nature. A smoker may light up a cigarette if he or she is feeling, for example, stressed at a particular moment. The physical and mental states of an addict—and the changes over time to those states—before, during, and after taking a drug are not able to be taken advantage of with current pharmacotherapies. This is because, on the time scales of interest, typically the delivery is effectively either only "instant" (e.g., a single intravenous injection) or constant (e.g. a passive transdermal patch). Similarly, the body's own responses change over the course of the day, as exemplified by circadian rhythms. Associated with these changes, different diseases seem to exhibit symptoms that rise and fall as a function of the time of day. Addictive behavior may be similarly affected.

Skin itself has a circadian rhythm, particularly for epidermal cell proliferation, perhaps due to its significant exposure to light. This is important to account for when designing transdermal drug delivery systems. Indeed, research has shown that nicotine clearances change by roughly 17% over the course of a day and 42% with meals. The researchers concluded that because of time-dependent kinetic changes, an ideal transdermal system would provide an initial high delivery rate, near constant output during the day, decreasing delivery rate throughout the night, and short increases following meals.

Thus, the programmability, remote re-programmability, the ability to perform combination drug therapy and incorporation of effective chemical enhances used with the transdermal patches disclosed in the present invention may provide for more effective controlled delivery regimens in a variety of environments for treating a variety of diseases and other medical conditions, such as but not limited to drug addictions, obesity, and risk for heart attack or stroke.

Thus, the present invention saves both time and money as a patient does not have to be transported to a hospital for every potential condition; ER staff and doctors do not have to repeatedly readmit a patient each time the patient arrives at the hospital; insurance/Medicaid and hospitals save money by not readmitting patients but rather by treating at home/remotely; the PCDSS application saves physician time by culling all relevant information and providing diagnoses/suggested courses of treatment; and physicians can still effectively monitor patients and modify treatment protocols or advise patients to become admitted to a hospital should the need arise. The present invention further saves time and money as patients can receive prescribed medications through a smart delivery system allowing for combination drug therapy and remote reprogramming of the device to modify or add medications without requiring a physician office visit.

Figure 7:
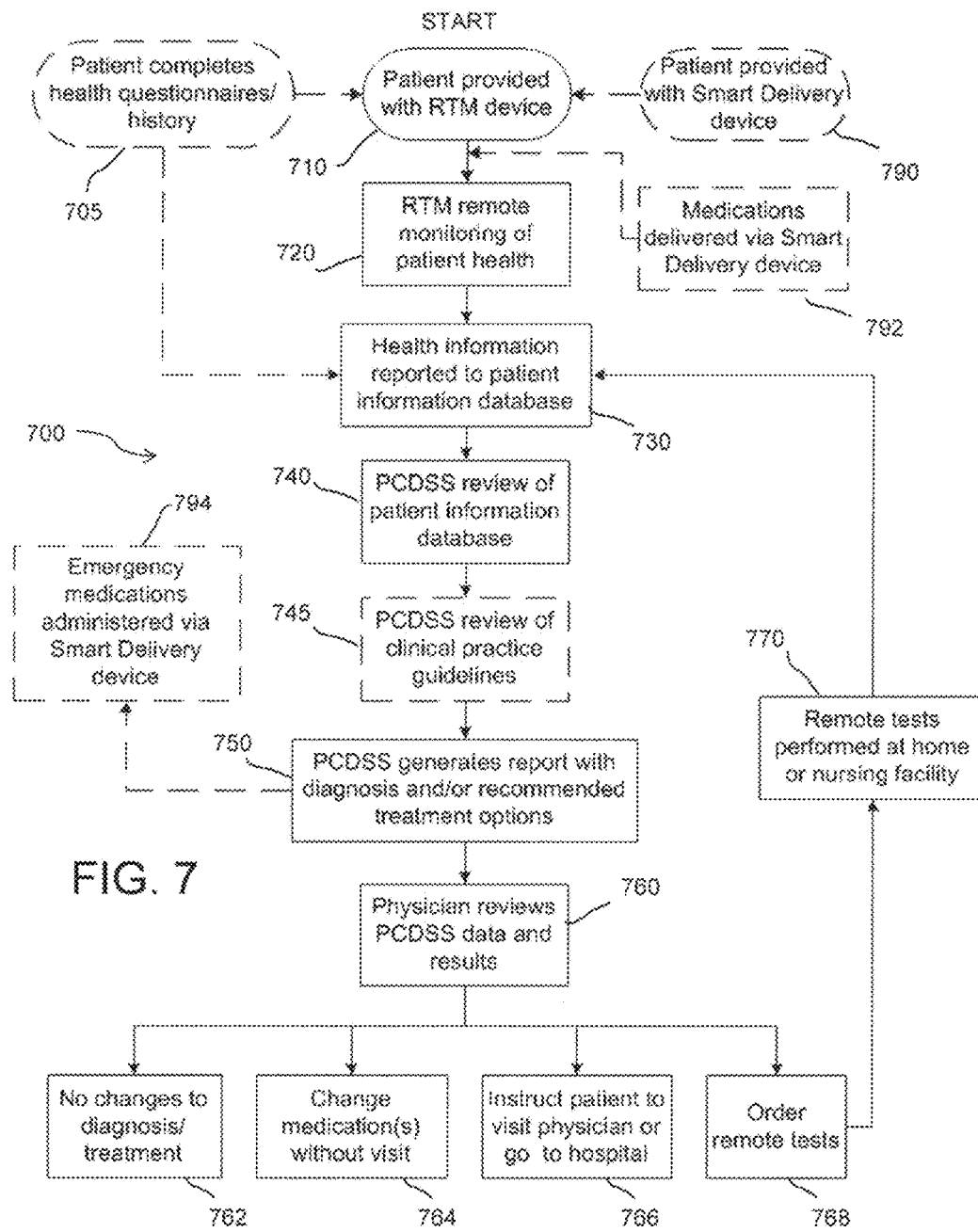
FIG. 7 is an exemplary flow diagram of a method utilizing the physician-centric health care delivery system of the present invention.

Having described some of the component devices and aspects that may be included in system 100, an exemplary flow diagram for a method utilizing the physician-centric health care delivery system of the present invention is shown in FIG. 7 and is generally indicated by reference numeral 700. In step 710, a patient is provided with a remote telehealth/telemedicine monitoring ("RTM") device and instructed in its use. The patient may receive the RTM device following a check-up at a doctor's office or upon discharge from a hospital. The RTM device permits the patient to monitor his or her vital signs or other doctor-recommended health parameters (e.g., blood glucose levels, blood oxygenation, heart rate, blood pressure, etc.) from the comfort of the patient's home or nursing facility (step 720). As described above, in step 730, the RTM device is enabled for wireless communication with server 110 (or enables transfer of information to an internet connected computing device) to provide immediate, real-time reading and recording of patient health statistics within the patient information database 115. A patient may optionally complete health questionnaires or medical history profiles (step 705), with such information also stored within the patient information database 115.

In step 740, the PCDSS interrogates the patient information stored within the patient information database to generate a report containing a preliminary diagnosis and/or a recommended course of treatment (step 750). As shown in optional step 745, the PCDSS can additionally access and utilize clinical practice guidelines ("CPGs") which pertain to the diagnosed condition (e.g., heart failure) as determined previously by a physician before the patient was released and provided with remote monitoring as in step 710 or as determined by the PCDSS when analyzing the current patient health information. CPGs help clinicians (and in the present invention the PCDSS application) make medical decisions by providing recommendations that are based on various levels of evidence and are integrated with other clinical information systems that offer case-specific advice. Assisting the physician in diagnosis of complex diseases requires a series of decisions that are often based on incomplete data. Thus, the algorithms used in the PCDSS managed by the physician-centric healthcare network delivery system of the present invention are based on a combination of the latest CPGs along with telemedicine to retrieve and monitor patient data on a daily basis.

Once a report is generated by the PCDSS (step 750), a physician can access and review that report through an internet enabled computing device (step 760). In accordance with the invention, a notice or other electronic warning is transmitted to the physician should the PCDSS determine a change in the patient's medical condition, as for example, a patient diagnosed with congestive heart failure is potentially about to suffer or is currently suffering a heart attack. Depending upon the PCDSS analysis of the patient data (with optional consultation to CPGs), the PCDSS recommends one or more of a multiple courses of action. For instance, one recommendation is to make no changes in the diagnosis or treatment regimen (step 762); or the PCDSS can recommend modification to the administration of medication(s) without requiring an in-person visit (step 764). A further recommendation is to instruct the patient to schedule an appointment to see the physician in person or for the patient to go directly to the hospital (step 766). A fourth recommendation (step 768) includes an order for additional medical tests, with these tests being conducted by a home health professional at the patient's home, nursing facility or other location without requiring the patient to be readmitted to a hospital. If remote tests are ordered and conducted (as in step 770), the test results are inputted into the patient information database where those results are then analyzed by the PCDSS application to issue a further report. In each case, the treating physician may accept, modify or choose to ignore the PCDSS generated recommendations. It is understood that, while in the example only four recommended courses of action are shown, the PCDSS contemplated by this invention may provide for any number of courses of action options that may be pertinent to proper treatment.

Method 700 may further include provisions wherein a patient in provided with a smart delivery device such as those described with reference to FIGS. 5, 6A and 6B above, but may also include smart delivery devices having IV or SC delivery systems. As shown in optional step 790, in addition to being provided with an RTM device (step 710), a patient is further provided with a smart delivery device. As indicated by step 792, the smart delivery device administers medications as per physician instruction. The smart delivery device may also, if indicated by the PCDSS and sensed data, dispense an emergency dosage of medication to stop or minimize the damages caused by an immediate medical crisis, such as a heart attack (step 794).

Thus, as can be seen by the description of the system and method of FIGS. 1 and 7, the PCDSS software application receives, interrogates and reports a patient's medical condition in real-time from the patient's home or nursing care facility through use of RTM device(s) without requiring a costly physician office or hospital emergency room visitation. Combined with the abilities of portable remote medical diagnostic tools (e.g., portable x-ray, ultrasound, etc.) the PCDSS system enables a treating physician to readmit only those patients who require hospitalization, while also enabling further treatment of patients (through medication modifications or remote testing) from the comfort of that patient's home or nursing facility. Provision of a smart delivery device further aids in remote medicine by programmably (and remotely reprogammably) administering prescribed medications to patients, and further enables immediate emergency dosing should the need arise.

Exemplary algorithms scripted for use by the PCDSS as described with regard to method 700 for diagnosing and/or treating a patient with congestive heart failure ("CHF") will be described with reference to FIGS. 8 and 9. It is to be understood that CHF is merely exemplary and not limiting and the PCDSS system of the present invention can be utilized with regard to any suitable medical condition. The algorithms used in the PCDSS for CHF managed by the physician-centric healthcare network delivery system are based on a combination of the latest clinical practice guidelines (CPGs) along with RTM to retrieve and monitor patient data on a daily basis. As an example: a patient's vital bio-data are recorded and analyzed on a daily basis to establish a patient's normal baseline. Any changes to the normal baseline, such as a rapid rise from the normal baseline in weight, heart rate, etc., could trigger the PCDSS application to issue a CHF detection and alert the physician to look for signs of CHF and quickly automate the CHF management protocol. Adding patient vital bio-data monitoring and detection parameters increases the robustness of the PCDSS and enables the physician to effectively manage the treatments for CHF patients which results in a significant reduction in hospitalizations and readmissions. For example, the PCDSS can automatically advise a patient to hold off on beta blocker medication (i.e. atenolol or metoprolol) when the PCDSS notices the patient's heart rate is below 50 and the PCDSS sends an automatic message to the physician network where a physician can then contact the patient.

Figure 8:
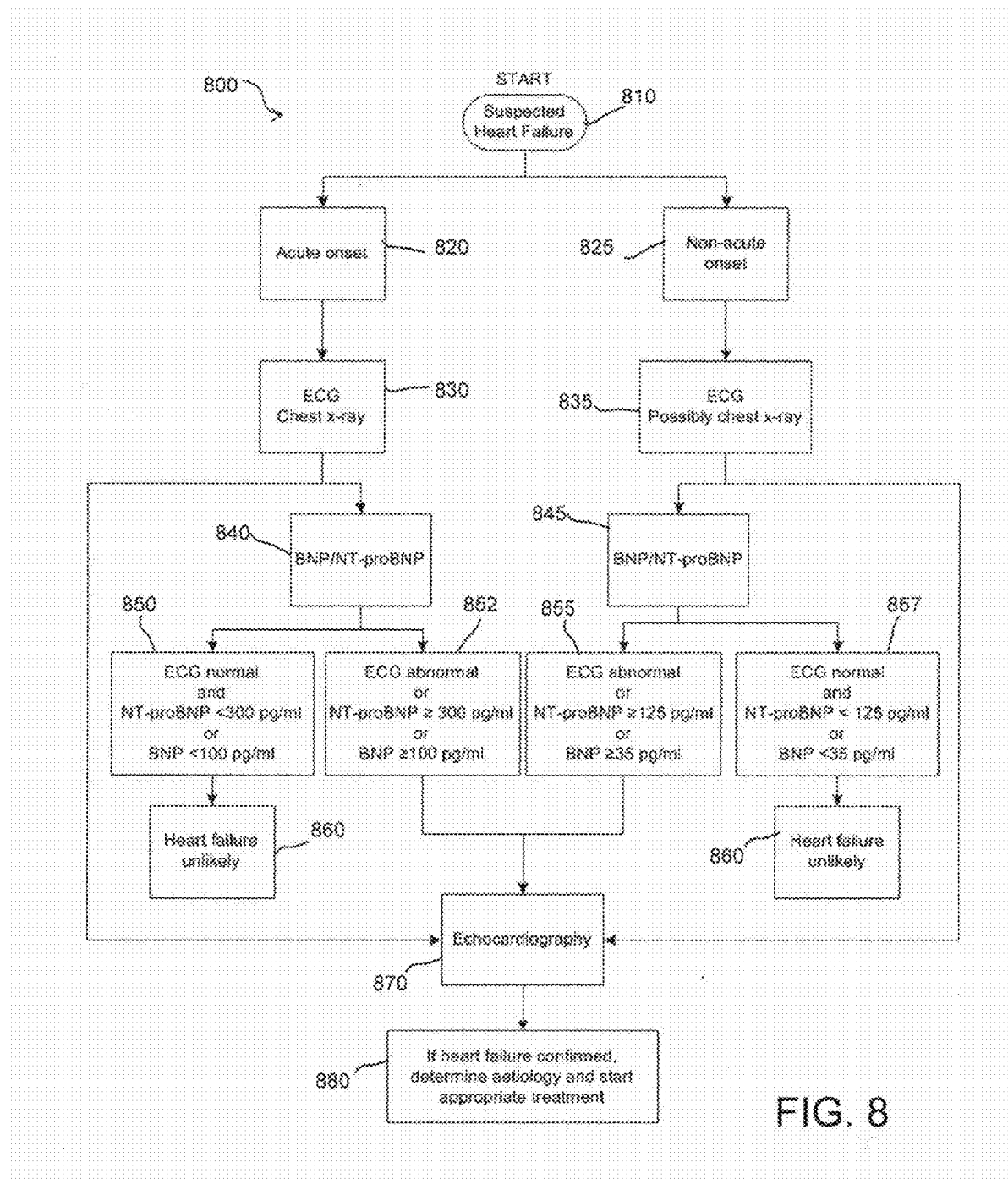
FIG. 8 is an exemplary flow diagram of an algorithm employed by the physician-centric health care delivery system of the present invention to determine the possible occurrence of heart failure.

Turning now specifically to FIG. 8, provided is an exemplary flow diagram of an algorithm 800 employed by the PCDSS of the present invention to determine the possible occurrence of heart failure. As discussed above with regard to FIG. 7, a patient is provided with an RTM device to remotely monitor vital signs and other health data. In the case of a patient with a history of heart failure or heart disease, the RTM monitors will likely measure a patient's weight, heart rate, blood pressure, pulse oxygenation and other criteria as determined by the treating physician. A patient may additionally complete questionnaires regarding his or her health condition. This may include daily logs as to the level of fatigue felt by the patient, any shortness of breath or difficulty breathing or whether there is swelling in the legs, each of which may be indicative of heart failure. Again, as provided above with regard to the method described with reference to FIG. 7, this data is transmitted and stored within a patient information database. The PCDSS via the CHF algorithm 800 interrogates the patient data to determine whether the patient is suffering potential heart failure. If a patient's vital statistics or answers to questionnaires indicate heart failure, the CHF algorithm 800 will be initiated in step 810. Algorithm 800 will review the medical data to determine if the onset of the heart failure was acute (step 820) or non-acute (step 825). In accordance with the invention, a notification will be sent to the treating physician (See FIG. 7, step 750) so that the treating physician can order remote testing. Alternatively, algorithm 800 may initiate setting up a mobile health professional visit automatically without the intervention of the treating physician. In the case of acute onset, algorithm 800 presents a recommendation that both an ECG and chest x-ray be conducted (step 830). If the onset was non-acute, the recommendation includes an ECG and possibly a chest x-ray whose need is determined by algorithm 800 through analysis of the probability of heart failure as indicated by the patient's medical history, or at the discretion of the treating physician (step 835).

Depending upon the severity of the results as determined by the ECG and, if ordered, the chest x-ray, algorithm 800 may immediately recommend an echocardiograph to more definitively confirm heart failure (step 870). If heart failure is not immediately indicated, algorithm 800, in steps 840 or 845, recommends to the physician (or automatically schedules) an appointment for further testing. A home health professional will withdraw a blood sample to conduct a test interrogating concentrations of B-type natriuretic peptide ("BNP") or N-terminal pro b-type natriuretic peptide ("NT-proBNP") in the blood, as these are indicative of heart failure. In steps 850, 852, 855 and 857, the concentrations of BNP or NT-proBNP are inputted into the patient information database and reviewed by the PCDSS. If the ECG (step 830 or 835) was normal and the BNP or NT-proBNP concentrations are not sufficiently high enough (steps 850 or 857), algorithm 800 presents a diagnosis that heart failure is unlikely (steps 860 or 865). However, if the ECG was abnormal or the BNP or NT-proBNP concentrations are greater than or equal a predetermined value (for instance, those defined within a CPG), algorithm 800 presents a recommendation for (or directly orders) an echocardiograph (steps 852 or 855). In step 870, an echocardiograph is conducted and if heart failure is confirmed, algorithm 800 presents a recommendation that the aetiology of the heart failure be determined and appropriate treatment be initiated (step 880).

Figure 9:
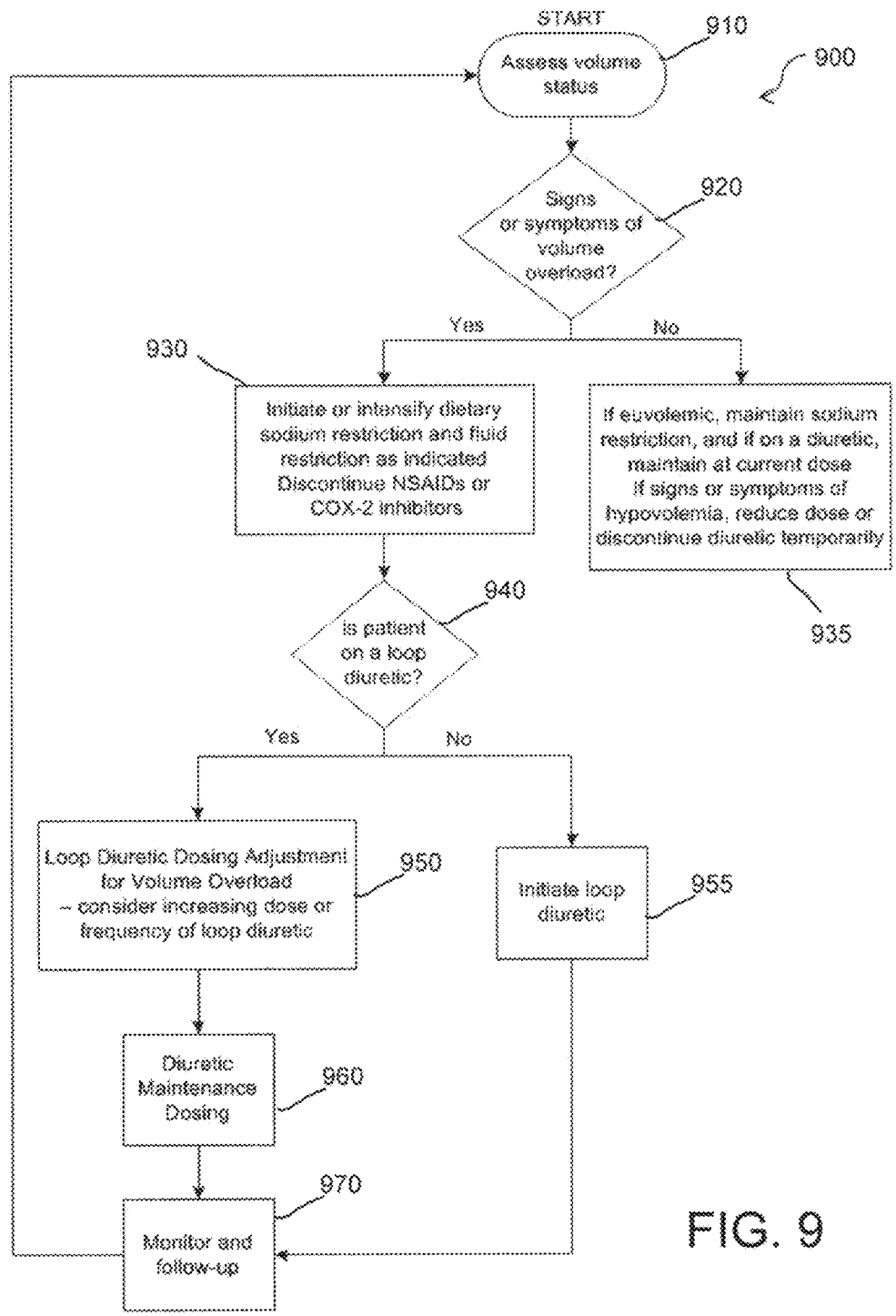
FIG. 9 is an exemplary flow diagram of an algorithm employed by the physician-centric health care delivery system to manage volume overload.

Turning now to FIG. 9, an exemplary flow diagram of an algorithm 900 employed by the PCDSS software to manage volume overload, or hypervolemia is shown. Congestive heart failure is a common result of hypervolemia. Symptoms of hypervolemia include increase in weight, swelling of the legs or arms, and shortness of breath. As provided by the method of the present invention, as discussed with reference to FIG. 7, RTM devices and patient questionnaires are used to remotely monitor the health condition of the patient. To monitor for hypervolemia, the PCDSS hypervolemia algorithm initiates communication with the RTM device and/or patient to assess the volume status of the patient's blood (step 910). These include monitoring blood pressure and pulse oxygenation via RTM or through targeted questions directed to the patient regarding identifying possible physical manifestations of hypervolemia. In step 920, the PCDSS hypervolemia algorithm reviews the data to determine if signs/information are present to indicate fluid overload.

As shown in step 935, if blood fluid levels are determined to be acceptable (euvolemic), the hypervolemia algorithm 900 will report and recommend that no changes be made to the patient's fluid regimen. If the patient is determined by the PCDSS algorithm to be hypervolemia (low blood volume), the hypervolemia algorithm 900 will report and recommend that the patient reduce or discontinue use of any diuretic. However, if the hypervolemia algorithm 900 reviews the patient information data and determines that volume overload is present, in step 930 the algorithm 900 will report and recommend the initiation or intensification of dietary sodium restriction and fluid restriction. Algorithm 900 will further recommend the patient discontinue use of any NSAIDs or COX-2 inhibitors.

Following the recommendations made in step 930, the hypervolemia algorithm 900 next reviews the patient information database to determine if the patient is currently receiving a loop diuretic (step 940). If the patient is not currently taking a loop diuretic, algorithm 900 reports and recommends the initiation of use of a loop diuretic (step 955). Once the loop diuretic is initiated, the patient's fluid volume status is monitored (step 970). If however, the patient is already using a loop diuretic, algorithm 900 reports and recommends diuretic dosing adjustment (step 950) to determine the proper dosing frequency or dose amount to maintain proper fluid levels which will then be maintained (step 960) and monitored (step 970) to ensure proper blood volumes.

Having described the system and method of the present invention and an embodiment thereof, an exemplary computer environment for implementing the described design and execution is presented next.

Figure 10:
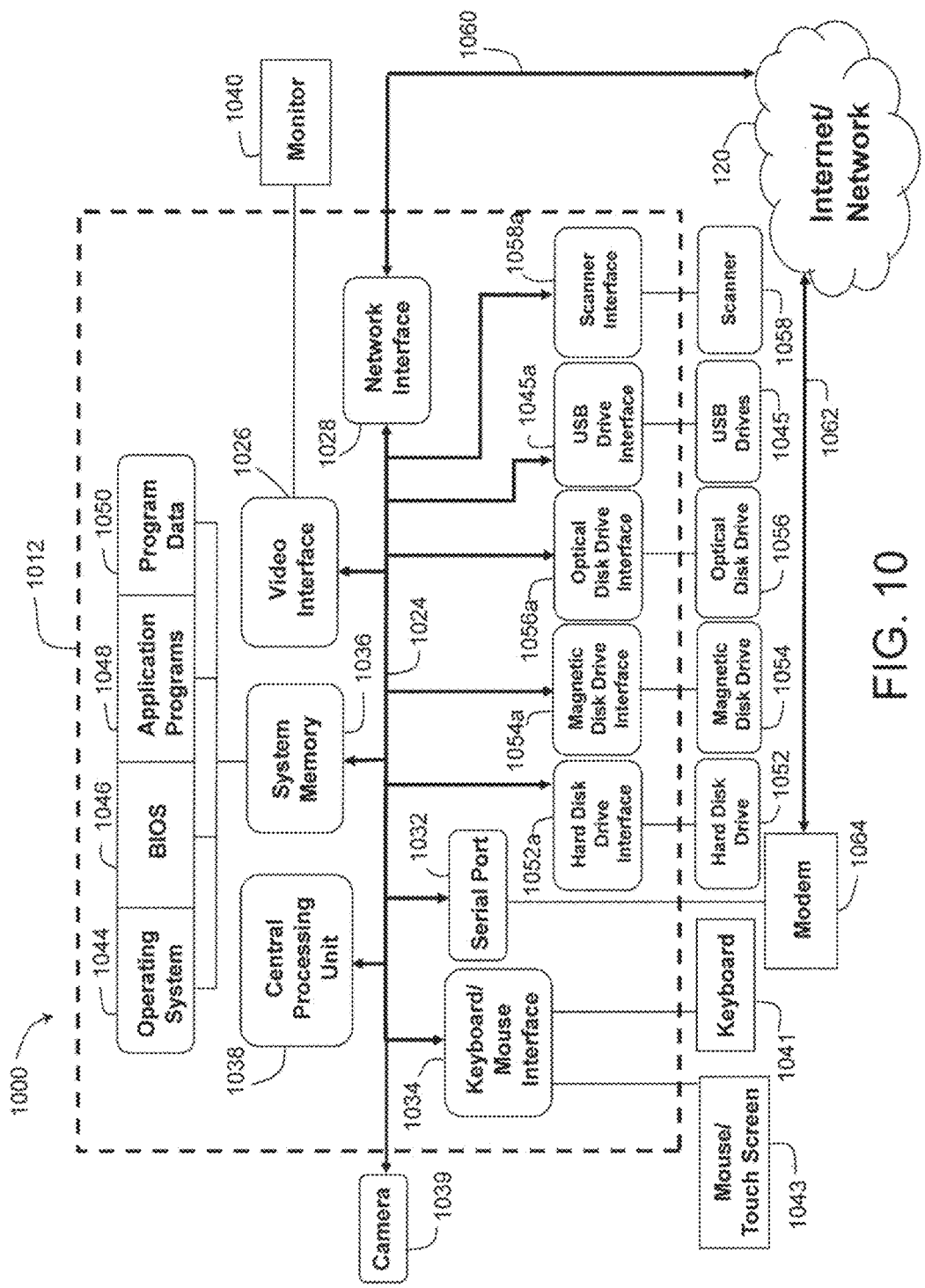
FIG. 10 is an exemplary computing environment that can be used to implement the physician-centric health care delivery system of the present invention.

FIG. 10 shows an exemplary computing environment 1000 that can be used to implement any of the processing thus far described. Computing environment 1000 may include one or more computing devices 1012 (such as any of computing devices 150 or 135) comprising a system bus 1024 that couples a video interface 1026, network interface 1028, a keyboard/mouse interface 1034, and a system memory 1036 to a Central Processing Unit (CPU) 1038. A monitor or display 1040 is connected to bus 1024 by video interface 1026 and provides the user with a graphical user interface that may be used to perform the steps of methods 700, 800 and/or 900 as described above. The graphical user interface allows the user to enter commands and information into computing device 1012 using a keyboard 1041 and a user interface selection device 1043, such as a mouse, touch screen, or other pointing device. Keyboard 1041 and user interface selection device are connected to bus 1024 through keyboard/mouse interface 1034. Additional interfaces may also be employed, such as but not limited to PS/2 and USB interfaces, and the like. The display 1040 and user interface selection device 1043 are used in combination to form the graphical user interface which allows the user to implement at least a portion of the present invention. Other peripheral devices may be connected to the remote computer through universal serial bus (USB) drives 1045, fire wire, network interface, and the like to transfer information to and from computing device 1012. For example, a camera 1039 may be connected to computer 150 through serial port 1032, USB drives 1045, or to bus 1024 through other equivalent ports so as to enable video capture during videoconference calls. Additional interfaces may also be employed, such as but not limited to PS/2 and USB interfaces, and the like.

The system memory 1036 is also connected to bus 1024 and may include read only memory (ROM), random access memory (RAM), an operating system 1044, a basic input/output system (BIOS) 1046, application programs 1048 and program data 1050. The computing device 1012 may further include a hard disk drive 1052 for reading from and writing to a hard disk, a magnetic disk drive 1054 for reading from and writing to a removable magnetic disk (e.g., floppy disk), and an optical disk drive 1056 for reading from and writing to a removable optical disk (e.g., CD ROM or other optical media). The computing device 1012 may also include USB drives 1045 and other types of drives for reading from and writing to flash memory devices (e.g., compact flash, memory stick/PRO and DUO, SD card, multimedia card, smart media xD card), and a scanner 1058 for scanning items to computing device 1012. A hard disk drive interface 1052a, magnetic disk drive interface 1054a, an optical drive interface 1056a, a USB drive interface 1045a, and a scanner interface 1058a operate to connect bus 1024 to hard disk drive 1052, magnetic disk drive 1054, optical disk drive 1056, USB drive 1045 and scanner 1058, respectively. Each of these drive components and their associated computer-readable media may provide remote computing device 1012 with non-volatile storage of computer-readable instruction, program modules, data structures, application programs, an operating system, and other data for computing device 1012. In addition, it will be understood that computing device 1012 may also utilize other types of computer-readable media in addition to those types set forth herein, such as digital video disks, random access memory, read only memory, other types of flash memory cards, magnetic cassettes, and the like.

Computing device 1012 may operate in a networked environment using logical connections with other computing devices. Network interface 1028 provides a communication path 1060 between bus 1024 and internet/network 120, which allows, for example, an RTM device or patient home computer to communicate data to the patient information database 115 via server 110, as well as enabling physicians to access the patient information database via computing device 150. This type of logical network connection is commonly used in conjunction with a local area network (LAN). The patient information files may also be communicated from bus 1024 through a communication path 1062 to internet/network 120 using serial port 1032 and a modem 1064. Using a modem connection between the computing device 1012 and other computing devices in the network is commonly used in conjunction with a wide area network (WAN). It will be appreciated that the network connections shown herein are merely exemplary, and it is within the scope of the present invention to use other types of network connections between computing device 1012 and other computing devices including both wired and wireless connections.

From the foregoing, it will be seen that this invention is one well adapted to attain all the ends and objects hereinabove set forth together with other advantages which are obvious and which are inherent to the method and apparatus. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. As used herein, the terms "having" and/or "including" and other terms of inclusion are terms indicative of inclusion rather than requirement.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

What is claimed is:

1. A system for diagnosing and treating a patient, the system comprising:

a patient information database for storing and retrieving patient health data related to the patient, the patient health data including real-time patient health information;

at least one server operative to access said patient information database;

a computing device remotely located from the server, the computing device configured to execute a physician-centric clinical support system application ("diagnostic computer application"), wherein the computing device is configured for communication with the server for retrieving the patient health data;

at least one remote telehealth/telemedicine device accessible to the patient configured for monitoring and generating the real-time patient health information and communicating the real-time patient health information generated to the server for storage within the patient information database, the real-time patient health information including blood pressure and pulse oxygenation before, during and after treatment;

the diagnostic computer application configured to generate a patient treatment recommendation using the retrieved patient health data including the real-time patient health information, the diagnostic computer application configured to process the patient health data for at least one clinical practice guideline for congestive heart failure to generate the patient treatment recommendation to remotely manage the congestive heart failure of the patient; and a drug delivery device remotely operative by a medical professional for real-time access to the patient health data including the real-time patient health information responsive to the patient treatment recommendation to dispense fluids in accordance with the patient treatment recommendation into the patient from the drug delivery device;

the drug delivery device comprising:
- an array of microneedles each configured with an out-of-plane configuration to penetrate skin of the patient for the delivery device worn in direct contact with the skin of the patient, the array of microneedles including micro-linear actuators configured for transdermal injections to less than one millimeter;
- a microfluidic chip having an array of microtubules with corresponding microfluidic channels respectively coupled to the array of microneedles for delivery of fluids from reservoirs of the drug delivery device to the array of microneedles for an array of different fluidic drugs for the fluids for the patient;
- a micro pump coupled to pump a selected fluid of the fluids from a reservoir of the reservoirs through a microfluidic channel of the microfluidic channels to a microneedle of the array of microneedles for the patient;
- a microcontroller in electrical communication with the micro pump to control operation of the micro pump to dispense the fluid in accordance with the patient treatment recommendation into the patient from the reservoir; and
- a heart rate sensor coupled to the microcontroller.

2. A system in accordance with claim 1, wherein:
the communication is over a network;
the at least one clinical practice guideline for the congestive heart failure includes a hypervolemia guideline to manage volume overload for managing the congestive heart failure of the patient via remote operation of the drug delivery device by the medical professional; and
the patient health data further includes one or more of at least one patient questionnaire and a patient medical history.

3. A system in accordance with claim 2, wherein the network is the Internet.

4. A system in accordance with claim 2, wherein the communication is wireless.

5. A system in accordance with claim 1, wherein the computing device is selected from a list comprising a personal desktop computer, a laptop computer, a tablet computing device and a smart device.

6. A system in accordance with claim 1, wherein the computing device further stores a scheduling computer application wherein execution of the scheduling computer application initiates a videoconference with the medical professional.

7. A method for diagnosing and treating a patient, the method comprising:
providing a patient information database for retrieving and storing patient health data related to the patient;
providing at least one server operative to access the patient information database;
providing at least one computing device remotely located from the server, the computing device configured to execute a physician-centric clinical support system application ("diagnostic computer application"), wherein the computing device is configured for communication with the server;
providing the patient with a remote telehealth/telemedicine device to monitor, generate and communicate real-time patient health information, the real-time patient health information including blood pressure and pulse oxygenation before, during, and after treatment and a heart rate sensor for monitoring the patient;
communicating the real-time patient health information to the patient information database for storage therein;
generating a patient treatment recommendation by executing the diagnostic computer application with the computing device based upon the real-time patient health information for at least one clinical practice guideline for congestive heart failure for remote management of the congestive heart failure of the patient; and
remotely controlling a dispensing of fluid in accordance with the patient treatment recommendation into the patient from a drug delivery device operative by a medical professional with real-time access to the patient health data including the real-time patient health information responsive to the patient treatment recommendation, the dispensing of the fluid comprising:
having the drug delivery device attached for direct contact with skin of the patient;
actuating a microneedle of the drug delivery device to penetrate skin of the patient for the drug delivery device worn in direct contact with the skin of the patient, the actuating including selecting a microneedle of an array of microneedles each configured with an out-of-plane configuration to penetrate skin of the patient for the delivery device worn in direct contact with the skin of the patient, the array of microneedles including micro-linear actuators configured for transdermal injections to less than one millimeter;
pumping the fluid through a microfluidic channel coupled to the microneedle for delivery of the fluid from a reservoir to the microneedle for the patient; and
the pumping including operating a micro pump under control of a microcontroller in electrical communication with the micro pump, the micro pump coupled to pump the fluid selected from fluids in reservoirs including the reservoir through the microfluidic channel of microfluidic channels corresponding to the array of microneedles to the microneedle to dispense the fluid in accordance with the patient treatment recommendation into the patient from the reservoir.

8. A method in accordance with claim 7, further comprising the steps of:
storing the at least one clinical practice guideline within the patient information database, the at least one clinical practice guideline including a hypervolemia guideline to manage volume overload for managing the congestive heart failure; and
storing one or more of at least one patient questionnaire or at least one patient medical history within the patient information database, wherein the at least one of the patient diagnosis or the patient treatment recommendation is generated by the diagnostic computer application based upon the real-time patient health information and the one or more of the at least one patient questionnaire or the at least one patient medical history for the at least one clinical practice guideline.

9. A method in accordance with claim 8, further comprising remotely instructing the patient by the diagnostic computer application to reduce or discontinue use of a diuretic.

10. A method in accordance with claim 8, further comprising remotely instructing the patient by the diagnostic computer application to initiate or intensify dietary sodium restriction and fluid restriction.

11. A method in accordance with claim 8, further comprising remotely instructing the patient by the diagnostic computer application to initiate or intensify dietary fluid restriction.

12. A method in accordance with claim 7, wherein the computing device further stores a scheduling computer application wherein execution of the scheduling computer application initiates a videoconference.

13. A system for diagnosing and treating a patient, the system comprising:
a telehealth/telemedicine device coupled to monitor, generate and communicate real-time patient health information before, during, and after treatment to a server for storage of the real-time patient health information in a patient information database;
a computing device remotely located from the server configured to execute a diagnostic application to retrieve patient health data from the patient information database;
the diagnostic computer application configured to generate a patient treatment recommendation using the patient health data including the real-time patient health information, the diagnostic computer application configured to process the patient health data for at least one clinical practice guideline for congestive heart failure to generate the patient treatment recommendation to remotely manage the congestive heart failure of the patient; and
a drug delivery device remotely operative by a medical professional for real-time access to the patient health data including the real-time patient health information responsive to the patient treatment recommendation to dispense fluid in accordance with the patient treatment recommendation into the patient from the drug delivery device, the drug delivery device comprising:
an array of microneedles each configured with an out-of-plane configuration to penetrate skin of the patient for the delivery device worn in direct contact with the skin of the patient, the array of microneedles including micro-linear actuators configured for transdermal injections to less than one millimeter;
a microfluidic chip having an array of microtubules with corresponding microfluidic channels respectively coupled to the array of microneedles for delivery of fluids from reservoirs of the drug delivery device to the array of microneedles for an array of different fluidic drugs for the fluids for the patient;
a micro pump coupled to pump a selected fluid of the fluids from a reservoir of the reservoirs through a microfluidic channel of the microfluidic channels to a microneedle of the array of microneedles for the patient;
a microcontroller in electrical communication with the micro pump to control operation of the micro pump to dispense the fluid in accordance with the patient treatment recommendation into the patient from the reservoir; and
a heart rate sensor coupled to the microcontroller.

14. The system according to claim 13, wherein the real-time patient health information includes blood pressure and pulse oxygenation for the patient.

* * * * *